(12) United States Patent
Choi et al.

(10) Patent No.: US 9,492,370 B2
(45) Date of Patent: Nov. 15, 2016

(54) COSMETIC COMPOSITION CARRIER CONTAINING URETHANE FOAM LAYER STRUCTURE

(71) Applicants: Jung Sun Choi, Yongin-si (KR); Kyung Nam Kim, Yongin-si (KR); (Continued)

(72) Inventors: Jung Sun Choi, Yongin-si (KR); Kyung Nam Kim, Yongin-si (KR); (Continued)

(73) Assignee: AMOREPACIFIC CORPORATION (KR)

( * ) Notice: Subject to any disclaimer, the term of this patent is extended or adjusted under 35 U.S.C. 154(b) by 0 days.

(21) Appl. No.: 14/371,658

(22) PCT Filed: Jan. 11, 2013

(86) PCT No.: PCT/KR2013/000229
§ 371 (c)(1),
(2) Date: Jul. 10, 2014

(87) PCT Pub. No.: WO01/00154
PCT Pub. Date: Jan. 4, 2001

(65) Prior Publication Data
US 2014/0341959 A1    Nov. 20, 2014

(30) Foreign Application Priority Data

Jan. 13, 2012 (KR) .................. 10-2012-0004479
Jan. 11, 2013 (KR) .................. 10-2013-0003163

(51) Int. Cl.
*A61K 8/87* (2006.01)
*A45D 34/00* (2006.01)
(Continued)

(52) U.S. Cl.
CPC ............... *A61K 8/87* (2013.01); *A45D 34/00* (2013.01); *A61K 8/0204* (2013.01);
(Continued)

(58) Field of Classification Search
CPC ................ A61K 8/0204; A61K 8/87; A61K 8/0208; A61K 2800/87; A61K
(Continued)

(56) References Cited

U.S. PATENT DOCUMENTS 4,186,445 A * 2/1980 Stager ................ A41D 19/0068
2/164
6,006,761 A   12/1999 Meledandri
(Continued)

FOREIGN PATENT DOCUMENTS

GB    1 498 363    * 1/1978
JP    08-164019       6/1996
(Continued)

OTHER PUBLICATIONS

European Search Report—EP13736154.9 dated Jul. 20, 2015.
(Continued)

*Primary Examiner* — Blessing M. Fubara
(74) *Attorney, Agent, or Firm* — Cantor Colburn LLP

(57) ABSTRACT

Disclosed are a cosmetic composition carrier containing a urethane foam layer structure, and cosmetics including the cosmetic composition carrier that contains a cosmetic composition.

14 Claims, 5 Drawing Sheets

(71) Applicants: Kyung Ho Choi, Yongin-si (KR);
Yeong Jin Choi, Yongin-si (KR)

(72) Inventors: Kyung Ho Choi, Yongin-si (KR);
Yeong Jin Choi, Yongin-si (KR)

(51) Int. Cl.
*A61Q 1/02* (2006.01)
*A61Q 19/00* (2006.01)
*A61K 8/02* (2006.01)

(52) U.S. Cl.
CPC ............ *A61K 8/0208* (2013.01); *A61Q 1/02* (2013.01); *A61Q 19/00* (2013.01); *A45D 2200/05* (2013.01); *A61K 2800/10* (2013.01); *A61K 2800/87* (2013.01)

(58) Field of Classification Search
CPC ............. 2800/10;A61Q 1/02; A61Q 19/00; A45D 34/00; A45D 2200/05
See application file for complete search history.

(56) References Cited

U.S. PATENT DOCUMENTS

| | | | |
|---|---|---|---|
| 2009/0148687 A1 | 6/2009 | Hirose et al. | |
| 2011/0014254 A1* | 1/2011 | Choi | A61K 8/0208 424/401 |

FOREIGN PATENT DOCUMENTS

| | | |
|---|---|---|
| JP | 2003-503334 | 1/2003 |
| JP | 2003-231197 | 8/2003 |
| KR | 10-0711182 | 4/2007 |
| KR | 1020090100643 | 9/2009 |
| WO | 01/00154 | 1/2001 |
| WO | 01/21501 | 3/2001 |
| WO | WO 01/21501 A1 * | 3/2001 |

OTHER PUBLICATIONS

International Search Report—PCT/KR2013/000229 dated Apr. 30, 2013.
Written Opinion—PCT/KR2013/000229 dated Apr. 30, 2013.

* cited by examiner

COSMETIC COMPOSITION CARRIER CONTAINING URETHANE FOAM LAYER STRUCTURE

TECHNICAL FIELD

The present disclosure relates to a carrier for a cosmetic composition comprising a layered structure of foamed urethane.

BACKGROUND ART

In general, liquid cosmetic compositions have been filled in vacuum containers, pump containers or glass containers to be distributed and stored. However, it is not thought that such containers have good portability. Recently, as users have required carrying out and modifying make-up even outdoors more and more, easily portable liquid cosmetic compositions have been increasingly on demand.

As a container for carrying liquid cosmetic compositions easily, there is a pact type container. To allow a liquid cosmetic composition to be contained in a pact type container, it is required to consider whether a carrier for a cosmetic composition is applicable to a pact type container or not, whether a cosmetic composition is packed sufficiently into the carrier or not, whether the carrier supports a cosmetic composition homogeneously for a long time or not, and whether an adequate amount of cosmetic composition is discharged from the carrier as desired or not, or the like. Therefore, there is a need for developing a carrier for a cosmetic composition applicable to a pact type container in view of the above.

REFERENCES OF THE RELATED ART (Patent Document 1) Korean Laid-Open Patent Publication No. 10-2009-0100643 (published on Sep. 24, 2009)

DISCLOSURE

Technical Problem

A technical problem to be solved by the present disclosure is to provide a carrier for a cosmetic composition which allows good packing of a cosmetic composition, supports a cosmetic composition homogeneously for a long time, enables an adequate amount of cosmetic composition to be discharged therefrom as desired, and maintains high durability even after supporting a cosmetic composition.

Another technical problem to be solved by the present disclosure is to provide a cosmetic product comprising the carrier for a cosmetic composition.

Technical Solution

In one general aspect, there is provided a carrier for a cosmetic composition comprising a layered structure of foamed urethane.

In another general aspect, there is provided a cosmetic product comprising the carrier for a cosmetic composition impregnated with a cosmetic composition.

Advantageous Effects

The carrier for a cosmetic composition according to an aspect of the present disclosure allows good packing of a cosmetic composition, supports a cosmetic composition homogeneously for a long time, enables an adequate amount of cosmetic composition to be discharged therefrom as desired, and maintains high durability even after supporting a cosmetic composition. Therefore, when using the carrier for a cosmetic composition according to an aspect of the present disclosure, it is possible for users to carry a liquid cosmetic composition easily, and thus to carry out make-up with ease even outdoors.

DETAILED DESCRIPTION

Figure 1:
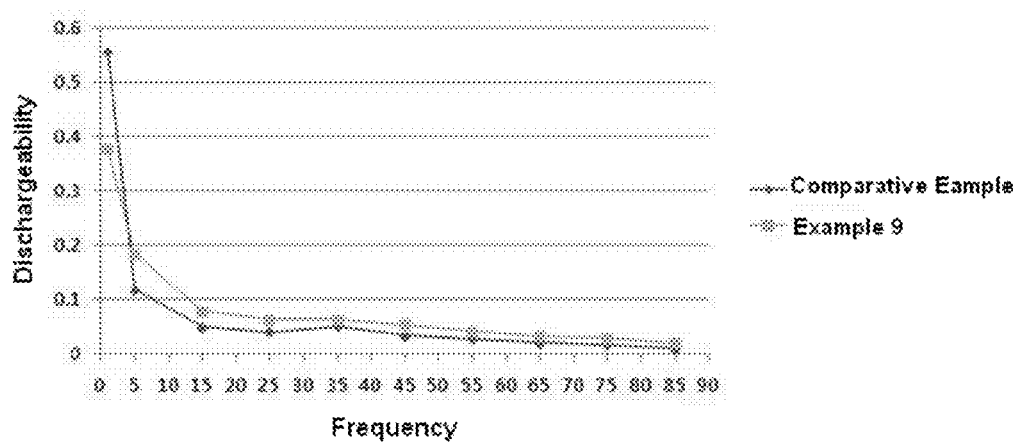
FIG. 1 is a graph illustrating the discharge amount of a cosmetic composition from the carrier for a cosmetic composition according to an aspect of the present disclosure as compared to the carrier for a cosmetic composition according to the related art.

In an aspect, the present disclosure provides a carrier for a cosmetic composition comprising a layered structure of foamed urethane. Although a carrier for a cosmetic composition comprising foamed urethane has been known per se previously, there is no disclosure about a carrier for a cosmetic composition having the layered structure as disclosed herein. The carrier for a cosmetic composition comprising foamed urethane according to the related art is problematic in that it shows a rapid drop in discharge amount of a cosmetic composition, after 50% or more of the cosmetic composition incorporated initially therein is taken out. On the contrary, the carrier for a cosmetic composition according to an aspect of the present disclosure comprises a layered structure of foamed urethane, and thus controls discharge of a cosmetic composition more uniformly from the start of use to the time of 50% or more of discharge, unlike the carrier for a cosmetic composition according to the related art.

As used herein, the term 'carrier' means one capable of supporting any material or ingredient, such as a composition, and is used exchangeably with 'supporting body', 'medium' or 'carrier body'. As used herein, the term 'supportability' means the ability of supporting and retaining any material or ingredient.

As used herein, the term 'foamed urethane' means foamed and solidified urethane and is referred to also as 'urethane foam'. According to an embodiment, foamed urethane comprises polyether-based foamed urethane. Polyether-based foamed urethane has a larger pore size, higher air permeability and higher cushioning property, softness, flexibility and elasticity, as compared to polyester-based foamed urethane.

According to another embodiment, foamed urethane may have a network structure having micropores. If it is a network structure, it supports a cosmetic composition more homogeneously with higher supporting efficiency as compared to a non-network structure.

The carrier for a cosmetic composition according to an aspect of the present disclosure may have a layered structure comprising multiple layers, particularly 2-20, more particularly 2-10, and even more particularly 2-5 layers.

According to still another embodiment, the layered structure of the carrier for a cosmetic composition comprises one or more foamed urethane layers, the foamed urethane layers being different from each other in at least one selected from the type of foamed urethane, pore number per inch of foamed urethane, pore size and layer thickness.

As used herein, foamed urethane comprises polyether-based foamed urethane, which comprises polyether-based dry foamed urethane and polyether-based wet foamed urethane. Particular types of foamed urethane used herein comprise such polyether-based dry foamed urethane and polyether-based wet foamed urethane. In general, wet foamed urethane has a smaller pore size than dry foamed urethane.

As used herein, 'pore' of foamed urethane means one present in foamed urethane having a network structure.

According to an embodiment, 'pore number' means the number of pores per inch of foamed urethane. The number of pores per inch may be 55 ppi-130 ppi, particularly 70 ppi-120 ppi, and more particularly 80 ppi-110 ppi. Herein, 'ppi' means the number of pores per inch. According to another embodiment, different types of foamed urethanes may have different pore numbers (i.e., pore numbers per inch). Particularly, foamed urethane having a relatively large pore number may have a number of pores per inch of 100 ppi-130 ppi, while foamed urethane having a relatively small pore number may have a number of pores per inch of 55 ppi-95 ppi. Both wet foamed urethane and dry foamed urethane have a pore number within the above-defined range.

As used herein, 'pore number' may be an average value obtained by measuring the number of pores present in 1 inch of width/length based on WI-QA-14 (ASTM standards) accurately.

When foamed urethane has a pore number larger than 130 ppi, it has poor elasticity, and thus it is difficult to control the fluidity, absorption or discharge of a cosmetic composition. When foamed urethane has a pore number less than 55 ppi, it shows degradation in supportability of a cosmetic composition after supporting the cosmetic composition.

As used herein, the term 'pore size' means an average diameter of pores of foamed urethane, and may be 500-900 μm, particularly 600-800 μm. When the pore size is less than 500 μm, the resultant carrier shows poor supporting and discharge quality. On the other hand, when the pore size exceeds 900 μm, the resultant carrier shows poor elasticity, and thus it is difficult to control the fluidity, absorption or discharge of a cosmetic composition.

As used herein, the term 'layer thickness' means the height of each foamed urethane layer. According to an embodiment, each layer of the carrier for a cosmetic composition may be 0.05 mm-30 mm, particularly 0.1 mm-10 mm, and more particularly 0.5 mm-2.0 mm. According to another embodiment, foamed urethane layers have different layer thicknesses. A foamed urethane layer having a relatively small thickness may have a thickness of 0.05 mm-0.15 mm. A foamed urethane layer having a relatively large thickness may have a thickness of 0.5 mm-3 mm. When foamed urethane layers have a thickness within the above-defined range, it is possible to obtain a desired effect, to satisfy both stability and safety of a carrier, and to realize high cost efficiency. Particularly, when foamed urethane layers have an excessively large thickness, a cosmetic composition is not discharged sufficiently. When foamed urethane layers have an excessively small thickness, it is not possible to discharge a cosmetic composition uniformly. According to still another embodiment, when an upper layer has an excessively large thickness, the effect derived from the presence of the lower layer is not provided sufficiently, and thus the desired overall effect of the layered structure disclosed herein is degraded. In this case, the upper layer affects more significantly upon the dischargeability of the carrier. Thus, it is important to control the thickness of the upper layer. According to yet another embodiment, the upper layer of the carrier for a cosmetic composition may have a thickness of 0.5 mm-2.5 mm, particularly 1 mm-2 mm.

As described above, the carrier for a cosmetic composition according to an aspect of the present disclosure comprises foamed urethane layers having different properties. As a result, the carrier for a cosmetic composition allows good packing of a cosmetic composition, supports a cosmetic composition homogeneously for a long time, enables an adequate amount of cosmetic composition to be discharged therefrom as desired, and maintains high durability even after supporting a cosmetic composition.

According to an embodiment, foamed urethane may have a density of 0.05-0.2 g/cm$^3$ (3.12-12.48 lb/ft$^3$), particularly 0.1-0.18 g/cm$^3$. When foamed urethane has a density less than 0.05 g/cm$^3$, it discharges an excessively large amount of cosmetic composition, thereby making it difficult to use the cosmetic composition with ease. When foamed urethane has a density larger than 0.2 g/cm$^3$, it is not possible to perform packing and discharge of a cosmetic composition sufficiently.

As used herein, the density may be a value measured by the method based on ASTM D3574.

According to an embodiment, when the carrier has a multilayer structure, the carrier has a hardness (i.e., ASKER hardness) of 55-100, particularly 80-100, as determined by DUROMETER HARDNESS METER F Type (available from ASKER). For example, the carrier has a hardness that is at least one value selected from 55, 60, 65, 70, 75, 80, 85, 90, 95 and 100. The multilayer carrier for a cosmetic composition may have a bilayer structure. When the multilayer carrier has a hardness less than 55, it shows poor packing ability and excessive dischargeability, and thus discharges an excessively large amount of cosmetic composition. When the multilayer carrier has a hardness more than 100, it shows poor packing ability and low dischargeability, and thus discharges an excessively small amount of cosmetic composition to provide a poor make-up effect.

According to another embodiment, the carrier for a cosmetic composition has two or more foamed urethane layers, and one of the foamed urethane layers may be compressed one obtained by hot pressing of polyether-based foamed urethane. Specifically, one of the layers may be one obtained by slicing polyether-based foamed urethane after foaming to obtain sponge with a thickness of 2-8 mm, particularly 4-6 mm, and more particularly 5 mm, and then compressing the sponge by hot pressing at a factor of 2-3, particularly 2.5. Particularly, the carrier for a cosmetic composition has a bilayer structure comprising two foamed urethane layers, wherein the upper layer of the bilayer structure is compressed polyether-based foamed urethane. Although there is no particular limitation in compressing methods, hot pressing may be used. When compressed, foamed urethane maintains the same pore number and has improved absorption and supporting quality, and thus discharges a cosmetic composition finely to realize controlled discharge.

When the carrier for a cosmetic composition has a bilayer structure comprising two foamed urethane layers, the bilayer structure may have polyether-based dry foamed urethane/polyether-based wet foamed urethane, polyether-based dry foamed urethane/polyether-based dry foamed urethane, polyether-based wet foamed urethane/polyether-based wet foamed urethane, or polyether-based wet foamed urethane/polyether-based dry foamed urethane. The bilayer structure may further comprise at least one nonwoven web layer.

The layered structure of the carrier for a cosmetic composition according to an aspect of the present disclosure may comprise a nonwoven web layer. According to an embodiment, the nonwoven web layer may comprise at least one selected from rayon, polyester, polyethylene (PE), polyethylene terephthalate (PET), polylactic acid (PLA), silk, bamboo fibers and cotton. In this case, since the carrier for a cosmetic composition further comprises a nonwoven web layer having ingredients different from the ingredients of a foamed urethane layer, it allows good packing of a cosmetic composition, supports a cosmetic composition homogeneously for a long time, enables an adequate amount of cosmetic composition to be discharged therefrom as desired, and maintains high durability even after supporting a cosmetic composition. According to an embodiment, the nonwoven web layer may comprise 50-80 wt % of rayon and 20-40 wt % of polyester based on the total weight of the nonwoven web layer. According to another embodiment, the nonwoven web layer may comprise 75-95 wt % of cotton and 5-25 wt % of polyethylene based on the total weight of the nonwoven web layer.

According to an embodiment, the nonwoven web forming the nonwoven web layer may have a weight of 30 g/m$^2$-100 g/m$^2$, particularly 65 g/m$^2$-80 g/m$^2$. When the nonwoven web has a weight less than 30 g/m$^2$, the nonwoven web layer has an irregular surface. When the nonwoven web has a weight greater than 100 g/m$^2$, it is not easy to pack and discharge a cosmetic composition.

According to an embodiment, the position of the nonwoven web layer is not particularly limited, and the nonwoven web layer may be the outermost layer or intermediate layer. For example, the carrier for a cosmetic composition may have a structure of nonwoven web/polyether-based dry foamed urethane, polyether-based dry foamed urethane/nonwoven web, nonwoven web/polyether-based wet foamed urethane, polyether-based wet foamed urethane/nonwoven web, nonwoven web/polyether-based dry foamed urethane/nonwoven web, nonwoven web/polyether-based wet foamed urethane/nonwoven web, polyether-based wet foamed urethane/nonwoven web/polyether-based wet foamed urethane, polyether-based wet foamed urethane/nonwoven web/polyether-based dry foamed urethane, polyether-based dry foamed urethane, polyether-based dry foamed urethane/nonwoven web/polyether-based wet foamed urethane, polyether-based dry foamed urethane/nonwoven web/polyether-based dry foamed urethane, or the like.

The layers forming the carrier for a cosmetic composition according to an aspect of the present disclosure may be sealed together by ultrasonic waves, heat, a binder or adhesive. Herein, sealing with a binder means bonding sealing in which a binder formulation is melted and dispersed onto the surfaces of foamed urethane layers so that the layers are bound to each other. Bonding sealing means bonding of a plurality of different sponge layers with an adhesive that is not harmful to the human body and has excellent adhesion. Ultrasonic sealing means bonding of a plurality of different sponge layers by irradiating ultrasonic waves to the bonding sites thereof.

Meanwhile, interlayer sealing generally uses a method of melting the surfaces of foamed urethane layers to integrate them. Hereby, in the carrier for a cosmetic composition according to an aspect of the present disclosure, the uppermost layer and the lowermost layer have the same ingredients, and the edges thereof are sealed together by ultrasonic waves, heat, a binder or adhesive so that the layers of the layered structure are bound to each other. In other words, according to an embodiment, there is provided a carrier for a cosmetic composition comprising at least two layers, particularly at least three layers. According to another embodiment, there is provided a carrier for a cosmetic composition having a layered structure, wherein the uppermost layer and the lowermost layer are nonwoven web layers and the intermediate layer disposed therebetween is a foamed urethane layer or nonwoven web layer. According to still another embodiment, there is provided a carrier for a cosmetic composition, wherein the uppermost layer and the lowermost layer are dry foamed urethane layers or wet formed urethane layers. In such carriers for a cosmetic composition, only the edges of the carriers are sealed, and thus the cosmetic composition is not affected by the sealing method. In addition, it is possible to avoid effects of the sealing method upon the skin.

The cosmetic composition applicable to the carrier for a cosmetic composition according to an aspect of the present disclosure may be a liquid composition. A liquid cosmetic composition has more difficulty in carrying and storing than a solid cosmetic composition. However, when using the carrier for a cosmetic composition according to an aspect of the present disclosure, even a liquid cosmetic composition may be carried and stored stably and safely. According to an embodiment, formulations of the cosmetic composition may comprise solution, emulsion or suspension, but are not limited thereto.

The cosmetic composition applicable to the carrier for a cosmetic composition according to an aspect of the present disclosure may be an emulsified composition, such as a water in oil (W/O) type or oil in water (O/W) type composition.

According to an embodiment, an emulsified cosmetic composition may have a low viscosity, particularly of 5,000-15,000 cps (centipoise), and more particularly of 6,000-10,000 cps. When an emulsified cosmetic composition has a viscosity less than 5,000 cps, oil phase/aqueous phase separation occurs right after preparing the emulsified cosmetic composition. As a result, it is difficult to impregnate urethane foam with such a composition. When an emulsified cosmetic composition has a viscosity higher than 15,000 cps, it provides an undesirable tacky and heavy touch feel during skin application.

According to an embodiment, the viscosity may be determined by a viscometer, LVDV II+PRO, spindle No. 63 at a spindle speed of 5 rpm.

According to an embodiment, the cosmetic composition may be formulated into make-up primer, make-up base, liquid or solid foundation, concealer, lipstick, lip gloss, powder, lip liner, eyebrow, eye shadow, blusher, twin cake, UV protector, lotion, cream, essence, or the like, but is not limited thereto.

In another aspect, the present disclosure provides a cosmetic product comprising the carrier for a cosmetic composition impregnated with a cosmetic composition. The cosmetic product comprises a cosmetic composition applied to the carrier for a cosmetic composition according to an aspect of the present disclosure. Therefore, the cosmetic product allows good packing of a cosmetic composition, supports a cosmetic composition homogeneously for a long time, enables an adequate amount of cosmetic composition to be discharged therefrom as desired, and maintains high durability even after supporting a cosmetic composition. In still another aspect, the cosmetic product may be provided as a cosmetic container generally called 'pack' in brief and comprising a container that has a bottom portion in which the carrier for a cosmetic composition is received, and a top portion as a lid to which a mirror or the like may be attached.

The examples, reference examples and test examples will now be described to describe the construction and effects of the present disclosure in more detail. The following examples, reference examples and test examples are for illustrative purposes only and not intended to limit the scope of the present disclosure.

Preparation Example

Preparation of W/O Type Emulsified Composition

A W/O type emulsified cosmetic composition is prepared by using the method generally known in the art. The cosmetic composition has a viscosity of 7,338 cps.

Example

Preparation and Evaluation of Carrier for Cosmetic Composition

Polyether-based dry foamed urethane, polyether-based wet foamed urethane, nonwoven web formed of 70% rayon and 30% polyester, and nonwoven web formed of 85% cotton and 15% polyethylene are used to provide a dry foamed urethane layer, wet foamed urethane layer or nonwoven web layer, respectively. The layers are sealed together to obtain a carrier for a cosmetic composition, and then the cosmetic composition obtained from Preparation Example is packed in the carrier. Then, the carrier impregnated with the cosmetic composition is evaluated for its ability of packing the cosmetic composition (packing ability), supporting the cosmetic composition homogeneously for a long time (supporting ability), discharging an adequate amount of cosmetic composition when users want to take the cosmetic composition therefrom (dischargeability), and its durability after packing the cosmetic composition. The packing ability (packing quality) is determined as the time for which 15 g of the cosmetic composition is packed, and the dischargeability (discharge quality) is determined as the amount of cosmetic composition taken when a user apply the composition packed in the carrier with puff once. The supporting ability (supporting quality) is determined as the amount of cosmetic composition retained in foam after packing 15 g of the cosmetic composition therein. In addition, bonding sealing used herein is bonding two different sponge layers with an adhesive that is not harmful to the human body and has excellent adhesion. Further, ultrasonic sealing is bonding two sponge layers by irradiating ultrasonic waves to the bonding sites of two different sponge layers.

The following Tables show the characteristics and evaluation results of the carriers for a cosmetic composition according to Examples 1-6.

TABLE 1

|  | Wet-Dry (Example 1) | Dry-Dry (Example 2) |
| --- | --- | --- |
| Description | Polyether-based dry foamed urethane (lower layer) + polyether-based wet foamed urethane (upper layer) | Polyether-based dry foamed urethane (lower layer) + polyether-based dry foamed urethane (upper layer) |
| Characteristics | Pore number: lower layer 110 ppi; upper layer 95 ppi | Pore number: lower layer 95 ppi; upper layer 110 ppi |
| Packing ability | ○ | ◎ |
| Supporting ability | ◎ | ◎ |
| Dischargeability | Δ | ◎ |
| Durability after applying composition | Maintain initial state after storing for a long time | Maintain initial state after storing for a long time |
| Sealing method | Bonding sealing and ultrasonic sealing | Bonding sealing |

TABLE 2

|  | Dry-Wet (Example 3) | Wet-Wet (Example 4) |
| --- | --- | --- |
| Description | Polyether-based wet foamed urethane (lower layer) + polyether-based dry foamed urethane (upper layer) | Polyether-based wet foamed urethane (lower layer) + polyether-based wet foamed urethane (upper layer) |
| Characteristics | Pore number: lower layer 95 ppi; upper layer 110 ppi | Pore number: lower layer 95 ppi; upper layer 110 ppi |
| Packing ability | ○ | Δ |
| Supporting ability | ◎ | ◎ |
| Dischargeability | ○ | Δ |
| Durability after applying composition | Maintain initial state after storing for a long time | Maintain initial state after storing for a long time |
| Sealing method | Bonding sealing and ultrasonic sealing | Bonding sealing and ultrasonic sealing |

TABLE 3

|  | Nonwoven Web-Foamed Urethane-Nonwoven Web (Example 5) | Nonwoven Web-Foamed urethane-Nonwoven Web (Example 6) |
| --- | --- | --- |
| Description | Polyether-based wet foamed urethane + nonwoven web of 70% rayon and 30% polyester | Polyether-based wet foamed urethane + nonwoven web of 85% cotton and 15% polyethylene |
| Characteristics | Nonwoven web uses superfine fibers with an absorptive capillary structure | Polyethylene of nonwoven web comprises 90 g of low-melting point fibers and 75 g |

TABLE 3-continued

| | Nonwoven Web-Foamed Urethane-Nonwoven Web (Example 5) | Nonwoven Web-Foamed urethane-Nonwoven Web (Example 6) |
|---|---|---|
| Packing ability | ○ | ○ |
| Supporting ability | ◎ | ◎ |
| Dischargeability | Δ | Δ |
| Sealing temperature | 200-250° C. | 90-120° C. |
| Sealing method | Heat sealing | Heat sealing |

As can be seen from the foregoing results, when each layer of the carrier for a cosmetic composition has a different composition (wet foamed urethane, dry foamed urethane or nonwoven web) or the foamed urethane of each layer has a different pore size, a cosmetic composition is packed well in the carrier, and the carrier supports the cosmetic composition homogeneously for a long time and discharges an adequate amount of cosmetic composition, and shows high durability after packing a cosmetic composition therein.

Test Example 1

Evaluation of Quality of Carriers Depending on Pore Number of Foamed Urethane

Carriers for a cosmetic composition having a layered structure comprising a foamed urethane layer are obtained in the same manner as the above Examples, except that polyether-based wet foamed urethane (RUBYCELL, Technoporous®) is used to form an upper layer and dry foamed urethane having a different pore number is used to form a lower layer. Each carrier is impregnated with the cosmetic composition according to Preparation Example and evaluated for its quality.

TABLE 4

Figure 2:
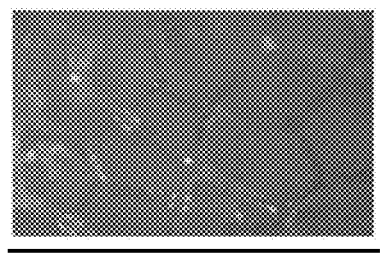
FIG. 2 is a microscopic image of lower layer of Reference Example 1.
Figure 3:
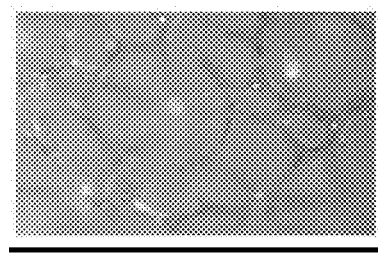
FIG. 3 is a microscopic image of lower layer of Example 7.
Figure 4:
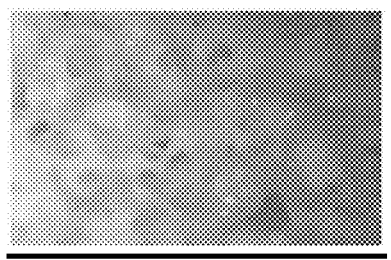
FIG. 4 is a microscopic image of lower layer of Reference Example 1.
Figure 5:
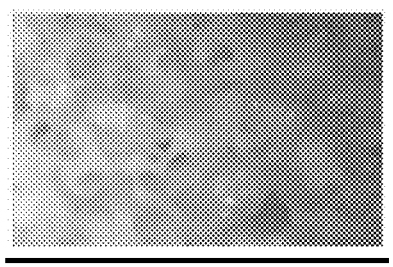
FIG. 5 is a microscopic image of lower layer of Example 7.

| | Reference Example 1 | Example 7 |
|---|---|---|
| Pore Number of Lower Layer Foamed Urethane | 40-50 ppi | 88-100 ppi |
| Density | 8.1-10.6 lb/ft³ | 8.1-10.6 lb/ft³ |
| Lower Layer Description | Polyether-based dry foamed urethane | Polyether-based dry foamed urethane |
| Microscopic Image of Lower Layer (Nikkon LU Plan Fluor) (5x/0.15A) | FIG. 2 | FIG. 3 |
| Microscopic Image of Upper layer (Nikkon LU Plan Fluor) (5x/0.15A) | FIG. 4 | FIG. 5 |
| Upper Layer Characteristics | Polyether-based wet foamed urethane (Technoporous ®) | Polyether-based wet foamed urethane (Technoporous ®) |
| Upper Layer Thickness | 2.5 mm | 2.5 mm |
| Packing Ability | ○ | ○ |
| Supporting Ability | X | ○ |
| Dischargeability | X | ○ |

As can be seen from the above results, the carrier for a cosmetic composition having a relatively larger number of pores per inch of a lower layer dry foamed urethane according to Example 7 shows better effects.

Test Example 2

Evaluation of Quality of Carriers Depending on Foamed Urethane Type and Layer Thickness Carriers for a cosmetic composition having a layered structure comprising a foamed urethane layer are obtained in the same manner as the above Examples, except that polyether-based foamed urethane having a network structure and a pore number of 95 ppi (pore per inch) is used to form a lower layer, and an upper layer is formed by varying ingredients and thickness. Each carrier is impregnated with the cosmetic composition according to Preparation Example and evaluated for its quality.

TABLE 5

Figure 6:
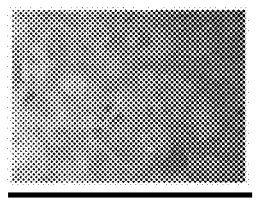
FIG. 6 is a microscopic image of lower layer of Reference Example 2.
Figure 7:
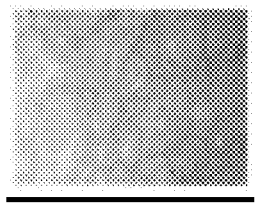
FIG. 7 is a microscopic image of upper layer of Reference Example 3.
Figure 8:
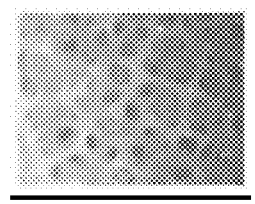
FIG. 8 is a microscopic image of upper layer of Example 8.

| | Reference Example 2 | Reference Example 3 | Example 8 |
|---|---|---|---|
| Pore Number of Lower Layer | 95 ppi | 95 ppi | 95 ppi |
| Lower Layer Description | Polyether-based dry foamed urethane | Polyether-based dry foamed urethane | Polyether-based dry foamed urethane |
| Microscopic Image of Upper Layer (Nikkon LU Plan Fluor) (5x/0.15A) | FIG. 6 | FIG. 7 | FIG. 8 |
| Upper Layer Description | Polyether-based wet foamed urethane (Technoporous ®) | Polyether-based dry foamed urethane (Supersoft ®) | Polyether-based wet foamed urethane |
| Upper Layer Thickness | 2.0 mm | 2.0 mm | 2.5 mm |
| Packing Ability | Easy packing | Easy packing | Easy packing |
| Supporting Ability | ○ | ○ | ○ |
| Dischargeability | X | X | ○ |
| Reference | | Cosmetic composition swells and flows out. Poor elasticity causes surface wrinkling. | |

As can be seen from the above results, it is possible to modify the effects of carriers for a cosmetic composition by controlling the type of upper layer foamed urethane, pore number per inch or thickness.

Test Example 3

Evaluation of Quality of Carriers Depending on Pore Size of Foamed Urethane

Carriers for a cosmetic composition having a layered structure comprising a foamed urethane layer are obtained in the same manner as the above Examples, except that polyether-based wet foamed urethane (RUBYCELL, Technoporous®) or polyether-based wet foamed urethane (RUBYCELL, Technoporous®) modified to have a larger pore size is used to form an upper layer, and dry foamed urethane is used to form a lower layer. Each carrier is impregnated with the cosmetic composition according to Preparation Example and evaluated for its quality.

TABLE 6

Figure 9:
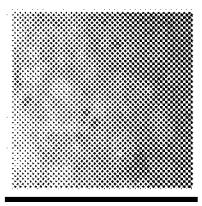
FIG. 9 is a microscopic image of upper layer of Reference Example 4.
Figure 10:
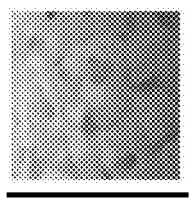
FIG. 10 is a microscopic image of upper layer of Example 9.
Figure 11:
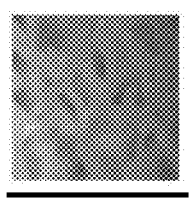
FIG. 11 is a microscopic image of upper layer of Example 10.

|  | Reference Example 4 | Example 9 | Example 10 |
|---|---|---|---|
| Pore Number of Lower Layer | 95 ppi | 95 ppi | 95 ppi |
| Lower Layer Description | Polyether-based dry foamed urethane having a network structure | Polyether-based dry foamed urethane having a network structure | Polyether-based dry foamed urethane having a network structure |
| Microscopic Image of Upper Layer (Nikkon LU Plan Fluor) (5x/0.15A) | FIG. 9 | FIG. 10 | FIG. 11 |
| Upper Layer Description | Polyether-based wet foamed urethane (Technoporous ®) Pore size 200pm-300 μm | Polyether-based wet foamed urethane (Technoporous ®) Pore size 500 μm-900 μm | Polyether-based wet foamed urethane (Technoporous ®) Pore size 500 μm-900 μm |
| Upper Layer Thickness | 2.0 mm | 2.5 mm | 2.0 mm |
| Upper Layer Density | 8.1-10.6 lb/ft$^3$ | 8.1-10.6 lb/ft$^3$ | 8.1-10.6 lb/ft$^3$ |
| Packing Ability | ○ | ○ | ○ |
| Dischargeability | X | ○ | ○ |

As can be seen from the above results, a larger pore size of upper layer foamed urethane improves the effect of a carrier for a cosmetic composition having a layered structure comprising a foamed urethane layer.

Test Example 4

Evaluation of Quality of Carriers Depending on Thickness of Foamed Urethane Layer Carriers for a cosmetic composition having a layered structure comprising a foamed urethane layer are obtained in the same manner as the above Examples, except that dry foamed urethane is used to form a lower layer and polyether-based wet foamed urethane (Technoporous®) modified to have a larger pore size is used to form an upper layer having a different thickness. Each carrier is impregnated with the cosmetic composition according to Preparation Example and evaluated for its quality.

TABLE 7

Figure 12:
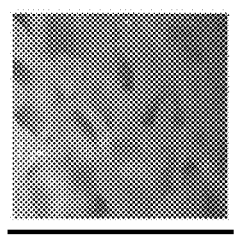
FIG. 12 is a microscopic image of upper layer of Example 11.
Figure 13:
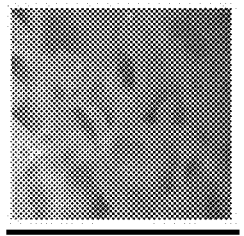
FIG. 13 is a microscopic image of upper layer of Example 12.

|  | Example 11 | Example 12 |
|---|---|---|
| Pore Number of Lower Layer | 95 ppi | 95 ppi |
| Lower Layer Description | Polyether-based dry foamed urethane having a network structure | Polyether-based dry foamed urethane having a network structure |
| Microscopic Image of Upper Layer (Nikkon LU Plan Fluor) (5x/0.15A) | FIG. 12 | FIG. 13 |
| Upper Layer Description | Polyether-based wet foamed urethane (Technoporous ®) Pore size 500 μm-900 μm | Polyether-based wet foamed urethane (Technoporous ®) Pore size 500 μm-900 μm |
| Upper Layer Thickness | 1.5 mm | 1.0 mm |
| Upper Layer Density | 8.1-10.6 lb/ft$^3$ | 8.1-10.6 lb/ft$^3$ |
| Packing ability | ○ | ○ |
| Dischargeability | ○ | ○ |

* In Tables 1-7, ◉ means 'very good', ○ means 'good', Δ means 'average', and X means 'poor.

As can be seen from the above results, Example 11 and Example 12 comprising an upper polyether-based wet foamed urethane layer with a thickness of 1-1.5 mm show higher dischargeability as compared to Example 7, Example 9 and Example 10 comprising an upper polyether-based wet foamed urethane layer with a thickness of 2-2.5 mm. Based on this, it can be seen that it is possible to improve the quality of the carrier for a cosmetic composition according to the present disclosure by controlling the thickness of a foamed urethane upper layer.

Test Example 5

Evaluation of Quality of Carriers Depending on Properties of Foamed Urethane Layer Carriers for a cosmetic composition having a layered structure comprising a foamed urethane layer are obtained in the same manner as the above Examples, except that polyether-based foamed urethane is sliced after foaming, and sponge with a thickness of 5 mm is compressed by hot pressing at a factor of 2.5 to form an upper layer. Each carrier is impregnated with the cosmetic composition according to Preparation Example and evaluated for its quality.

TABLE 8

Figure 14:
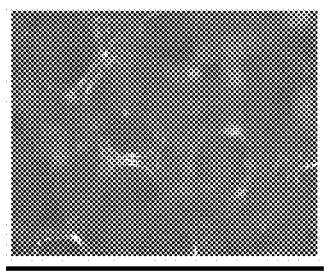
FIG. 14 is a microscopic image of monolayer of Reference Example 5.
Figure 15:
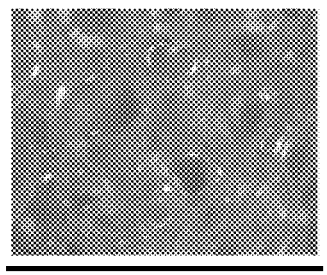
FIG. 15 is a microscopic image of upper layer of Example 13.

|  | Reference Example 5 | Example 13 |
|---|---|---|
| Carrier Structure | Monolayer | Bilayer |
| Carrier Description | Polyether-based dry foamed urethane having a network structure | Polyether-based dry foamed urethane having a network structure; bilayer structure wherein the lower layer is the same as monolayer, and the upper layer is compressed by hot pressing |
| Pore Number | 88-100 ppi | — |
| Pore Number of Lower Layer | — | 88-100 ppi |
| Lower Layer description | — | Polyether-based dry foamed urethane having a network structure |
| Microscopic Image (Nikkon LU Plan Fluor) (5x/0.15A) | Monolayer FIG. 14 | Upper layer FIG. 15 |
| Upper Layer Description | — | Polyether-based dry foamed urethane foam compressed by hot pressing |
| Carrier Thickness | 10.0 mm | 10.0 mm |
| Upper Layer Thickness | — | 2.0 mm |
| Carrier Density | 1.8-2.0 lb/ft$^3$ | — |
| Upper Layer Density | — | 4.5-5.0 lb/ft$^3$ |
| Packing Ability | ○ | ○ |
| Dischargeability | ○ | ○ |

Test Example 6

Evaluation of Uniform Dischargeability

A carrier for a cosmetic composition comprising a monolayer of polyether-based foamed urethane is prepared as Comparative Example. Example 9 is provided as a carrier for a cosmetic composition comprising a bilayer of polyether-based foamed urethane. Comparative Example and Examples 9 and 13 are impregnated with the W/O type emulsified cosmetic composition and introduced into a container. Then, the cosmetic composition is discharged from each carrier and the dischargeability is evaluated according to frequency. The results are shown in the following Table 9 and FIG. 1. The dischargeability shown hereinafter is the amount of cosmetic composition discharged each time when the total cosmetic composition supported on the carrier is taken as 1.

In Table 9, 'pay-off number' means the number of taking the cosmetic composition from each carrier, 'initial' means a pay-off number of 1-25, 'middle' means a pay-off number of 35-55, and 'late' means a pay-off number of 65-85.

TABLE 9

| Stage | Pay-off Number | Dischargeability of Comparative Example | Dischargeability of Example 9 | Dischargeability of Example 13 |
|---|---|---|---|---|
| Initial | 1 | 0.5563 | 0.3761 | 0.4021 |
|  | 5 | 0.1180 | 0.1830 | 0.2287 |
|  | 15 | 0.0492 | 0.0780 | 0.1453 |
|  | 25 | 0.0403 | 0.0632 | 0.1028 |
| Middle | 35 | 0.0503 | 0.0630 | 0.0973 |
|  | 45 | 0.0337 | 0.0532 | 0.00821 |
|  | 55 | 0.0276 | 0.0420 | 0.0665 |
| Late | 65 | 0.0206 | 0.0330 | 0.0450 |
|  | 75 | 0.0164 | 0.0280 | 0.0340 |
|  | 85 | 0.0098 | 0.0198 | 0.0230 |

As can be seen from the above results, the carrier for a cosmetic composition having a layered structure according to an aspect of the present disclosure discharges a cosmetic composition uniformly for a longer time as compared to the monolayer type carrier for a cosmetic composition according to the related art. Therefore, the carrier allows users to take a constant amount of cosmetic composition for a long time during use.

The invention claimed is:

1. A carrier for a cosmetic composition comprising two or more layers of foamed urethane,
wherein the two or more layers of foamed urethane are impregnated with a cosmetic composition, wherein the cosmetic composition is discharged from the carrier to a puff,
wherein the foamed urethane comprises polyether-based foamed urethane,
wherein the layers of foamed urethane are different from each other in at least one selected from the type of foamed urethane, number of pores per inch of foamed urethane, pore size and layer thickness.

2. The carrier for a cosmetic composition according to claim 1, wherein the foamed urethane has a network structure.

3. The carrier for a cosmetic composition according to claim 1, wherein the type of foamed urethane comprises dry foamed urethane or wet foamed urethane.

4. The carrier for a cosmetic composition according to claim 1, wherein the number of pores per inch of foamed urethane is 55 ppi-130 ppi (pore per inch).

5. The carrier for a cosmetic composition according to claim 1, wherein the pore size of foamed urethane is 500-900 μm.

6. The carrier for a cosmetic composition according to claim 1, wherein the layer thickness of foamed urethane is 0.05 mm-30 mm.

7. The carrier for a cosmetic composition according to claim 1, which comprises at least two layers of foamed urethane, wherein any one of the foamed urethane layers is compressed polyether-based foamed urethane.

8. The carrier for a cosmetic composition according to claim 7, wherein the compressed polyether-based foamed urethane is obtained by hot pressing.

9. The carrier for a cosmetic composition according to claim 1, which further comprises a nonwoven web layer.

10. The carrier for a cosmetic composition according to claim 9, wherein the nonwoven web comprises at least one of rayon, polyester, polyethylene, polyethylene terephthalate, polylactic acid, silk, bamboo fibers and cotton.

11. The carrier for a cosmetic composition according to claim 1, which comprises at least two layers and the uppermost layer and the lowermost layer are sealed together by ultrasonic waves, heat, a binder or adhesive.

12. The carrier for a cosmetic composition according to claim 1, wherein the cosmetic composition comprises a liquid composition.

13. The carrier for a cosmetic composition according to claim 1, wherein the cosmetic composition comprises a water-in-oil (W/O) type or oil-in-water (O/W) type composition.

14. A cosmetic product comprising the carrier for a cosmetic composition as defined in claim 1, impregnated with a cosmetic composition.

* * * * *